United States Patent [19]

Aoki

[11] 4,342,741

[45] Aug. 3, 1982

[54] DENTIFRICE COMPOSITIONS

[75] Inventor: Hideki Aoki, Kukizakimura, Japan

[73] Assignee: Dental Chemical Co., Ltd., Tokyo, Japan

[21] Appl. No.: 257,981

[22] Filed: Apr. 27, 1981

[51] Int. Cl.$^3$ .............................................. A61K 7/16
[52] U.S. Cl. ....................................... 424/57; 424/49
[58] Field of Search .................................. 424/57, 49

[56] References Cited

U.S. PATENT DOCUMENTS 4,048,300  9/1977  Tomlinson et al. .............. 424/57 X

*Primary Examiner*—Shep K. Rose
*Attorney, Agent, or Firm*—Paul and Paul

[57] ABSTRACT

A dentifrice composition containing synthetic hydroxyapatite powder preferably in an amount of from 5 to 60% by weight and being slightly or weakly acidic preferably having a pH of from 4 to 6.9. The dentifrice composition is very effective in eliminating plaque from tooth surfaces and also has a high fortifying and remineralizing effect on the tooth surfaces.

2 Claims, 6 Drawing Figures

DENTIFRICE COMPOSITIONS

The invention relates to dentifrice compositions.

According to the present invention, there is provided a dentifrice composition containing synthetic hydroxyapatite powder and being slightly or weakly acidic. The synthetic hydroxyapatite powder is preferably contained in the composition in an amount of 5 to 60% by weight based on the weight of the composition.

It has been found that the dentifrice composition of the present invention is effective in eliminating plaque (a colong of bacteria) from a tooth surface and also has high fortifying and remineralizing effects on the enamel coating of the tooth.

In general, a conventional dentifrice contains, as a tooth-cleaning and abrading agent, a mineral such as colloidal silica, calcium phosphate, calcium carbonate, magnesium carbonate and the like. It has heretofore been considered that while these abrading agents are used to remove contaminants from teeth, it is essential that they do not harm the teeth. Therefore, the abrading agents incorporated in conventional dentifrices have only slight ability to abrade the teeth.

However, it has now been found that it is not important, for the prevention of tooth decay, that the dentifrice does not abrade the teeth, but it is necessary, for the effective elimination of plaque from the tooth surface, that the dentifrice abrades the teeth, with some slight force. The dentifrice composition of the present invention can afford a moderate and effective abrading action to the enamel coating of the tooth, through the presence of an appropriate amount of the synthetic hydroxyapatite powder. It is presumed that this is due to the fact that the synthetic hydroxyapatite has a hardness similar to that of the enamel portion of the tooth and, thus, can impart an appropriate abrading effect on the enamel portion during brushing of the teeth. It has further been found that the dentifrice composition of the present invention containing synthetic hydroxyapatite powder can promote the coating or remineralization of the enamel surface of the tooth to fortify the surface of the tooth.

In order to attain a moderate abrading effect, it is preferable that the synthetic hydroxyapatite powder has an average particle size of about $2\mu$ and a maximum particle size of $10\mu$ or less. If the particle size is too large the abrading effect is too high, while if the particle size is too small no abrading effect can be expected.

The dentifrice composition of the present invention is slightly or weakly acidic, the preferred pH value being in a range of from 4 to 6.9. Thus, the dentifrice composition can easily eliminate plaque which up to now has been difficult to eliminate by using conventional dentifrices which are usually neutral or weakly alkaline, and thus, cannot effectively prevent the teeth from decaying. The acidity of the dentifrice composition may be attained by adding a non-toxic acid such as phosphoric acid, citric acid or lactic acid and these acids may preferably be employed in a buffer solution.

The dentifrice composition of the present invention may easily be prepared by a process comprising blending synthetic hydroxyapatite powder with an organic matrix and adding an acid to make the composition slightly or weakly acidic. Any organic matrixes generally employed in conventional dentifrices may be employed. To the organic matrix, there may be added any conventional tooth-cleaning and abrading agents. However, it may be appreciated that it is essentially unnecessary to add such a tooth-cleaning and abrading agent to the dentifrice composition of the present invention.

The "synthetic hydroxyapatite" as used herein refers to the stoichiometric hydroxyapatite obtained by synthesis.

The present invention will further be illustrated by the following non-limitative examples. Examples 1 through 7 show formulations of the dentifrice compositions according to the present invention in terms of parts by weight and Example 8 shows comparisons of the compositions of the present invention to a conventional dentifrice composition.

EXAMPLE 1

| Tooth Paste | |
|---|---|
| Hydroxyapatite powder | 10.0 |
| Calcium phosphate | 25.0 |
| CMC sodium salt | 0.3 |
| Carrageenin | 1.2 |
| Glycerin | 10.0 |
| Sorbitol | 15.0 |
| Sodium lauryl sulphate | 2.0 |
| Flavour | 1.2 |
| Sodium saccharinate | 0.1 |
| Silicon dioxide | 2.0 |
| Lactic acid | 0.2 |
| Sodium phosphate | 1.0 |
| Water | 30.0 |

This composition has a pH value of about 5.0.

EXAMPLE 2

| Tooth Paste | |
|---|---|
| Hydroxyapatite powder | 5.0 |
| Calcium phosphate | 10.0 |
| Calcium pyrophosphate | 20.0 |
| CMC sodium salt | 1.0 |
| Sodium alginate | 0.1 |
| Glycerin | 10.0 |
| Sorbitol | 10.0 |
| Sodium lauryl sulphate | 1.5 |
| Sodium lauryl sarcosinate | 0.5 |
| Flavour | 0.5 |
| Sodium saccharinate | 0.1 |
| Silicon dioxide | 2.5 |
| Citric acid | 2.0 |
| Lactic acid | 0.2 |
| Sodium phosphate | 1.0 |
| Water | 35.0 |

EXAMPLE 3

| Tooth Paste | |
|---|---|
| Hydroxyapatite powder | 20.0 |
| Calcium pyrophosphate | 10.0 |
| CMC sodium salt | 0.5 |
| Carrageenin | 0.6 |
| Glycerin | 20.0 |
| Sorbitol | 10.0 |
| Sodium lauryl sulphate | 2.0 |
| Flavour | 1.0 |
| Sodium saccharinate | 0.1 |
| Silicon dioxide | 2.0 |
| Citric acid | 2.0 |
| Lactic acid | 0.3 |
| Sodium phosphate | 0.5 |
| Water | 30.0 |

EXAMPLE 4

| Tooth Paste | |
| --- | --- |
| Hydroxyapatite powder | 35.0 |
| CMC sodium salt | 1.0 |
| Carrageenin | 0.3 |
| Glycerin | 35.0 |
| Sodium lauryl sulphate | 2.0 |
| Flavour | 1.0 |
| Sodium saccharinate | 0.1 |
| Silicon dioxide | 2.5 |
| Citric acid | 2.0 |
| Lactic acid | 0.1 |
| Sodium phosphate | 1.0 |
| Water | 20.0 |

EXAMPLE 5

| Tooth Powder | |
| --- | --- |
| Hydroxyapatite powder | 38.0 |
| Sodium pyrophosphate | 50.0 |
| Silicon dioxide | 5.0 |
| Sodium lauryl sulphate | 2.0 |
| Flavour | 2.0 |
| Sodium saccharinate | 0.3 |
| Citric acid | 2.0 |
| Potassium phosphate | 0.7 |

EXAMPLE 6

| Wet Tooth Powder | |
| --- | --- |
| Hydroxyapatite powder | 63.0 |
| Calcium phosphate | 10.0 |
| Sorbitol | 10.0 |
| Sodium lauryl sulphate | 2.0 |
| Flavour | 1.5 |
| Citric acid | 2.0 |
| Lactic acid | 0.38 |
| Potassium phosphate | 1.0 |
| Water | 10.0 |
| Sodium saccharinate | 0.12 |

EXAMPLE 7

Abrasive test pieces of a disc shape with a diameter of 8 mm and a thickness of 2 mm were prepared using a silver alloy (having a hardness similar to that of a tooth and consisting of silver 65%, tin 22% and zinc 13%.) The test pieces were abraded, immediately before the abrasive test, with Emery papers of up to #2000 to obtain a smooth and plane surface. The abrasive test was carried out using a disc-type abrading machine with a low rotating speed, at an abrading speed of 25 m/min for 2 minutes, by placing cow leather on the disc, applying a dentifrice composition to be tested onto the leather and pressing the test piece to the leather at a load of 300 g. The weight decrease of the test piece was measured for each composition.

Then, the test piece was subjected to the measurement of surface roughness and the measured surface roughness was recorded.

The tested compositions were the tooth paste as described in Example 4 wherein the hydroxyapatite powder having a particle size of from 2 to $10\mu$ (No. 2) and hydroxyapatite powder having a particle size of from 10 to $100\mu$ (No. 3). Further, a commercially available dentifrice (WHITE & WHITE) was used as a control (No. 1).

The measured weight decreases of the respective compositions were as follows.

| No. 1 | 0.45 mg |
| --- | --- |
| No. 2 | 0.30 mg |
| No. 3 | 3.28 mg |

Further, the surface roughness shown in FIGS. 1 through 3, in which FIG. 1 (A) shows the surface roughness before the abrasive test for composition No. 1 and FIG. 1 (B) shows the surface roughness after the abrasive test for composition No. 1. Likewise, FIGS. 2 (A) and (B) show the surface roughness before and after the abrasive test, respectively, and FIGS. 3 (A) and (B) show the surface roughness before and after the abrasive test, respectively. It is apparent from these figures that the dentifrice composition according to the present invention is very effective in smoothing the tooth surface.

I claim:

1. A dentifrice composition for toothpaste having a pH of from 4 to 6.9 and consisting essentially of:
   30 to 35 parts by weight of an abrading agent containing 5 to 25 parts by weight of synthetic hydroxyapatite powder and the balance of at least one member selected from the group consisting of calcium phosphate and calcium pyrophosphate;
   20 to 35 parts by weight of at least one filler selected from the group consisting of glycerin and sorbitol; and
   20 to 35 parts by weight of water.

2. A dentifrice composition as claimed in claim 1, wherein the synthetic hydroxyapatite powder has an average particle size of about $2\mu$ and a maximum particle size of $10\mu$ or less.

* * * * *